(12) United States Patent
Yang et al.

(10) Patent No.: US 12,195,471 B2
(45) Date of Patent: Jan. 14, 2025

(54) SALT OF ALDOSE REDUCTASE INHIBITOR, AND PREPARATION METHOD AND APPLICATION THEREOF

(71) Applicant: CSPC ZHONGQI PHARMACEUTICAL TECHNOLOGY (SHIJIAZHUANG) CO., LTD., Hebei (CN)

(72) Inventors: Zhankun Yang, Hebei (CN); Hanyu Yang, Hebei (CN); Pengfei Li, Hebei (CN); Xiaopeng Liu, Hebei (CN); Caihong Zhou, Hebei (CN); Junling Wang, Hebei (CN); Chunna Li, Hebei (CN); Xibao Liu, Hebei (CN)

(73) Assignee: CSPC ZHONGQI Pharmaceutical Technology (Shijiazhuang) Co., Ltd., Hebei (CN)

( * ) Notice: Subject to any disclaimer, the term of this patent is extended or adjusted under 35 U.S.C. 154(b) by 720 days.

(21) Appl. No.: 17/434,591

(22) PCT Filed: Feb. 28, 2020

(86) PCT No.: PCT/CN2020/077233
§ 371 (c)(1),
(2) Date: Aug. 27, 2021

(87) PCT Pub. No.: WO2020/173495
PCT Pub. Date: Sep. 3, 2020

(65) Prior Publication Data
US 2022/0127273 A1    Apr. 28, 2022

(30) Foreign Application Priority Data
Feb. 28, 2019  (CN) .......................... 201910152719.X

(51) Int. Cl.
C07D 487/04    (2006.01)
(52) U.S. Cl.
CPC ........ C07D 487/04 (2013.01); C07B 2200/13 (2013.01)
(58) Field of Classification Search
CPC .................................................. C07D 487/04

USPC ......................................................... 544/236
See application file for complete search history.

(56) References Cited

U.S. PATENT DOCUMENTS 4,939,140 A * 7/1990 Larson ................. C07D 417/12
                                                  544/80
5,304,557 A    4/1994 Mylari

FOREIGN PATENT DOCUMENTS

| CN | 103052637 A | 4/2013 |
|---|---|---|
| CN | 105121414 A | 12/2015 |
| WO | 2014/126885 A1 | 8/2014 |
| WO | 2019/023648 A1 | 1/2019 |

OTHER PUBLICATIONS

Bastin et al., Salt selection and optimisation procedures for pharmaceutical new chemical entities[J]. Organic Process Research & Development, 2000, 4(5): 427-435.
Caira M R. Crystalline polymorphism of organic compounds[J]. Design of Organic Solids, 1998: 163-208.
Kümmerer K. Pharmaceuticals in the environment[J]. Annual review of environment and resources, 2010, 35: 57-75.
Morissette, et al. High-throughput crystallization: polymorphs, salts, co-crystals and solvates of pharmaceutical solids[J]. Advanced drug delivery reviews, 2004, 56(3): 275-300.
Serajuddin Salt formation to improve drug solubility[J]. Advanced drug delivery reviews, 2007, 59(7): 603-616.
International Search Report in PCT/CN2020/077233, mailed May 19, 2020, 4 pages.

* cited by examiner

*Primary Examiner* — Taofiq A Solola
(74) *Attorney, Agent, or Firm* — Kilpatrick Townsend & Stockton LLP

(57) ABSTRACT

The present invention sets forth a salt of an aldose reductase inhibitor shown in formula A-N. The salt being able to be prepared as a crystal form, having notably improved solubility relative to the compound of formula A, having lower hygroscopicity allowing for stable existence, and thus being more easily made into a medicine than are the formula A compound or other salts.

10 Claims, 3 Drawing Sheets

SALT OF ALDOSE REDUCTASE INHIBITOR, AND PREPARATION METHOD AND APPLICATION THEREOF

TECHNICAL FIELD

The invention belongs to the field of pharmaceutical chemistry, and particularly relates to a salt of an aldose reductase inhibitor, and a preparation method and application thereof.

BACKGROUND TECHNOLOGY

Diabetes is one of the most common chronic conditions. High blood glucose levels result from a lack of insulin production and/or insulin sensitivity. Individuals with high blood glucose metabolize more glucose via a glucose to sorbitol to fructose pathway in insulin insensitive cells such as lenses, peripheral nerves, and glomerulus. This leads to an overabundance of sorbitol in the cells, which is not easily diffused through the cell membrane. The increased concentration of sorbitol triggers an influx of water into the cells, causing swelling and potential damage.

Aldose reductase, an enzyme present in many parts of the body, catalyzes the reduction of glucose to sorbitol, one of the steps in the sorbitol pathway that is responsible for fructose formation from glucose. Aldose reductase activity increases as the glucose concentration rises in diabetic conditions where tissues are no longer insulin sensitive. These tissues include, for example, lenses, peripheral nerves, and glomerulus of the kidney. Sorbitol cannot easily diffuse through cell membranes and therefore accumulates, causing osmotic damage, which in turn leads to retinopathy, neuropathy, and nephropathy. Therefore, inhibition of aldose reductase could prevent the buildup of sorbitol in insulin insensitive cells in diabetic, and presents a novel method to prevent the macrovascular and microvascular complications in diabetic patients. In addition, aldose reductase inhibitors, such as zopolrestat, may aid in treating or ameliorating such effects and have shown efficacy in wound healing in the corneal epithelium of diabetic animal models.

Chinese invention patent CN201180034944.5 discloses an aldose reductase inhibitor represented by the following formula I:

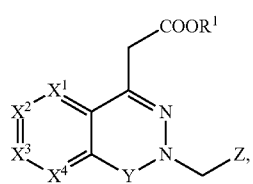

Wherein Examples 1 and 2 disclose the compound having the following structure:

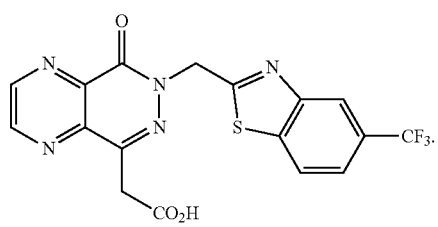

SUMMARY OF THE INVENTION

The present inventors have found that the compound of formula A is insoluble in water, which seriously affects its druggability. Therefore, it is necessary to modify the structure of the compound of formula A to meet the requirement of the medicament manufacture.

To solve the above problems, the present invention provides a compound represented by the formula A-N,

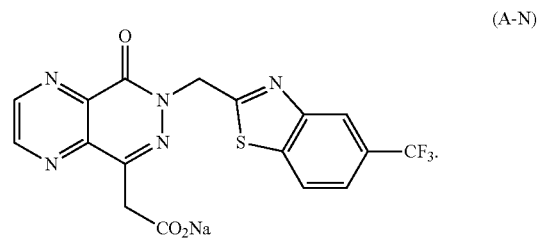

In some embodiments, the compound represented by formula A-N has an infrared spectrum, expressed as the reciprocal of the wavelength ($cm^{-1}$), with absorption peaks at 1675.5, 1611.0, 1379.6, 1333.4, 1152.6, and 1119.1.

In some embodiments, the compound represented by formula A-N is in a crystal form.

In some embodiments, a crystal form of the compound represented by formula A-N is characterized by an X-ray powder diffraction with characteristic peaks at 17.2±0.2°, 21.4±0.2°, 21.9±0.2°, and 25.9±0.2° expressed with 2θ angles by using the Cu—Kα radiation.

In some embodiments, a crystal form of the compound represented by formula A-N is characterized by an X-ray powder diffraction with characteristic peaks at 7.1±0.2°, 12.5±0.2°, 17.2±0.2°, 21.4±0.2°, 21.9±0.2°, 24.1±0.2°, and 25.9±0.2° expressed with 2θ angles by using the Cu—Kα radiation.

In some embodiments, a crystal form of the compound represented by formula A-N is characterized by an X-ray powder diffraction with characteristic peaks at 7.1±0.2°, 10.1±0.2°, 10.9±0.2°, 12.5±0.2°, 13.7±0.2°, 14.4±0.2°, 17.2±0.2°, 19.4±0.2°, 21.4±0.2°, 21.9±0.2°, 24.1±0.2°, and 25.9±0.2° expressed with 2θ angles by using the Cu—Kα radiation.

In some embodiments, a crystal form of the compound represented by formula A-N is characterized by an X-ray powder diffraction with characteristic peaks at 7.1±0.2°, 10.1±0.2°, 10.9±0.2°, 12.5±0.2°, 13.7±0.2°, 14.4±0.2°, 17.2±0.2°, 19.4±0.2°, 21.4±0.2°, 21.9±0.2°, 24.1±0.2°, 25.9±0.2°, 27.6±0.2°, and 30.6±0.2° expressed with 2θ angles by using the Cu—Kα radiation.

In some embodiments, said crystal form of the compound represented by formula A-N has an X-ray powder diffraction spectrum (XRPD) substantially as shown in FIG. 1.

In some embodiments, said crystal form of the compound represented by formula A-N begins to significantly decompose at 260-270° C.

In some embodiments, said crystal form of the compound represented by formula A-N has a DSC-TGA curve substantially as shown in FIG. 2.

The present invention also provides a method for preparing the compound represented by formula A-N, comprising the following steps:

Suspending the compound represented by formula A in water, adding an aqueous solution of an alkaline sodium compound to perform a salt-forming reaction, separating solids, and drying to obtain the compound represented by formula A-N.

The compound of formula A of the present invention can be prepared with reference to the methods described in Examples 1 and 2 of patent document CN201180034944.5.

According to the preparation method of the present invention, the alkaline sodium compound is selected from: sodium hydroxide, sodium carbonate, sodium bicarbonate, sodium methoxide, sodium ethoxide, sodium acetate, and sodium formate, preferably sodium hydroxide, sodium carbonate, and sodium bicarbonate, and more preferably sodium carbonate and sodium bicarbonate.

According to the preparation method of the present invention, the aqueous solution of the alkaline sodium compound can be of any appropriate concentration, and preferably has a mass volume concentration of 1-50%, more preferably 5-20%, for example 5%, 10%, or 20%.

According to the preparation method of the present invention, the molar ratio of the alkaline sodium compound to the compound of formula A is 1-3:1, preferably 1-1.5:1, and more preferably 1-1.1:1, wherein the mole number of the alkaline sodium is on a univalent basis.

According to the preparation method of the present invention, the temperature, at which the aqueous solution of the alkaline sodium compound is added, is 0-50° C., preferably 10-40° C., and more preferably 10-25° C.

According to the preparation method of the present invention, the reaction temperature of the salt-forming reaction is 20-80° C., preferably 40-70° C., and more preferably 60-65° C.

According to the preparation method of the present invention, the mass volume ratio of the compound of formula A to water is 1:5-50, preferably 1:5-20, and more preferably 1:10-20.

According to the preparation method of the present invention, after the reaction is finished, the temperature is cooled to −5° C. to 10° C., the crystallization is stood for 8-24 hours, the solid is separated and dried, and the above-mentioned crystal form of the compound represented by formula A-N is obtained.

According to the preparation method of the present invention, the separation step comprises separating the obtained crystal of the compound represented by formula A-N from the crystallization liquid with a suitable process such as filtration, centrifugation, or the like.

According to the preparation method of the present invention, the drying process may employ any suitable known process, preferably, drying under a reduced pressure (in vacuum). The specific drying conditions include, for example, the drying temperature is preferably 40-70° C., more preferably 45-65° C.; the pressure is preferably vacuum degree>0.090 MPa; the drying time is preferably 10-50 hours, more preferably 20-40 hours. No matter what drying process is used, it is desired that the residual amount of the solvent in the obtained product meets the quality standard.

In another aspect, the present invention also relates to a pharmaceutical composition containing the above-mentioned compound represented by formula A-N.

In yet another aspect, the present invention also relates to the use of the above-mentioned compound represented by formula A-N or the above-mentioned pharmaceutical composition containing the compound represented by formula A-N in manufacture of a medicament, wherein said medicament is useful in inhibiting the activity of an aldose reductase in a subject, for example, promoting healthy aging of skin, the treatment of skin disorders, the treatment of angiogenesis disorders such as cancers, the treatment of tissue damage, the treatment of cardiovascular disorders, the treatment of renal disorders, the treatment of evolving myocardial infarction, and the treatment of various other disorders, such as complications arising from diabetes. Such disorders may include but are not limited to, atherosclerosis, coronary artery disease, diabetic nephropathy, diabetic neuropathy, diabetic retinopathy, skin infection, peripheral vascular disease, stroke, and the like.

In yet another aspect, the present invention also relates to the above-mentioned compound represented by formula A-N or the above-mentioned pharmaceutical composition containing the compound represented by formula A-N for use in inhibiting the activity of an aldose reductase in a subject, for example, promoting healthy aging of skin, the treatment of skin disorders, the treatment of angiogenesis disorders such as cancers, the treatment of tissue damage, the treatment of cardiovascular disorders, the treatment of renal disorders, the treatment of evolving myocardial infarction, and the treatment of various other disorders, such as complications arising from diabetes. Such disorders may include but are not limited to, atherosclerosis, coronary artery disease, diabetic nephropathy, diabetic neuropathy, diabetic retinopathy, skin infection, peripheral vascular disease, stroke, and the like.

In yet another aspect, the present invention also relates to a method of treating disorders in a patient by administering to the patient the above-mentioned compound represented by formula A-N or the above-mentioned pharmaceutical composition containing the compound represented by formula A-N, the treatment of disorders in the patient is to inhibit the activity of an aldose reductase in the patient, for example, promoting healthy aging of skin, the treatment of skin disorders, the treatment of angiogenesis disorders such as cancers, the treatment of tissue damage, the treatment of cardiovascular disorders, the treatment of renal disorders, the treatment of evolving myocardial infarction, and the treatment of various other disorders, such as complications arising from diabetes. Such disorders may include, but are not limited to, atherosclerosis, coronary artery disease, diabetic nephropathy, diabetic neuropathy, diabetic retinopathy, skin infection, peripheral vascular disease, stroke, and the like.

The above "subject" and "patient" include all members of the animal kingdom, including, but not limited to, mammals (e.g., mice, rats, cats, monkeys, dogs, horses, pigs, etc.) and human.

Advantageous Effects

The present invention provides a sodium salt of the compound of formula A. The present inventors have surprisingly found that the salt can be prepared in a crystal form, which has significantly improved solubility relative to the compound of formula A, has low hygroscopicity and can exist stably, thus being easier to be formed into a medicament relative to the compound of formula A or other salts of the compound of formula A.

DETAILED DESCRIPTION

Figure 1:
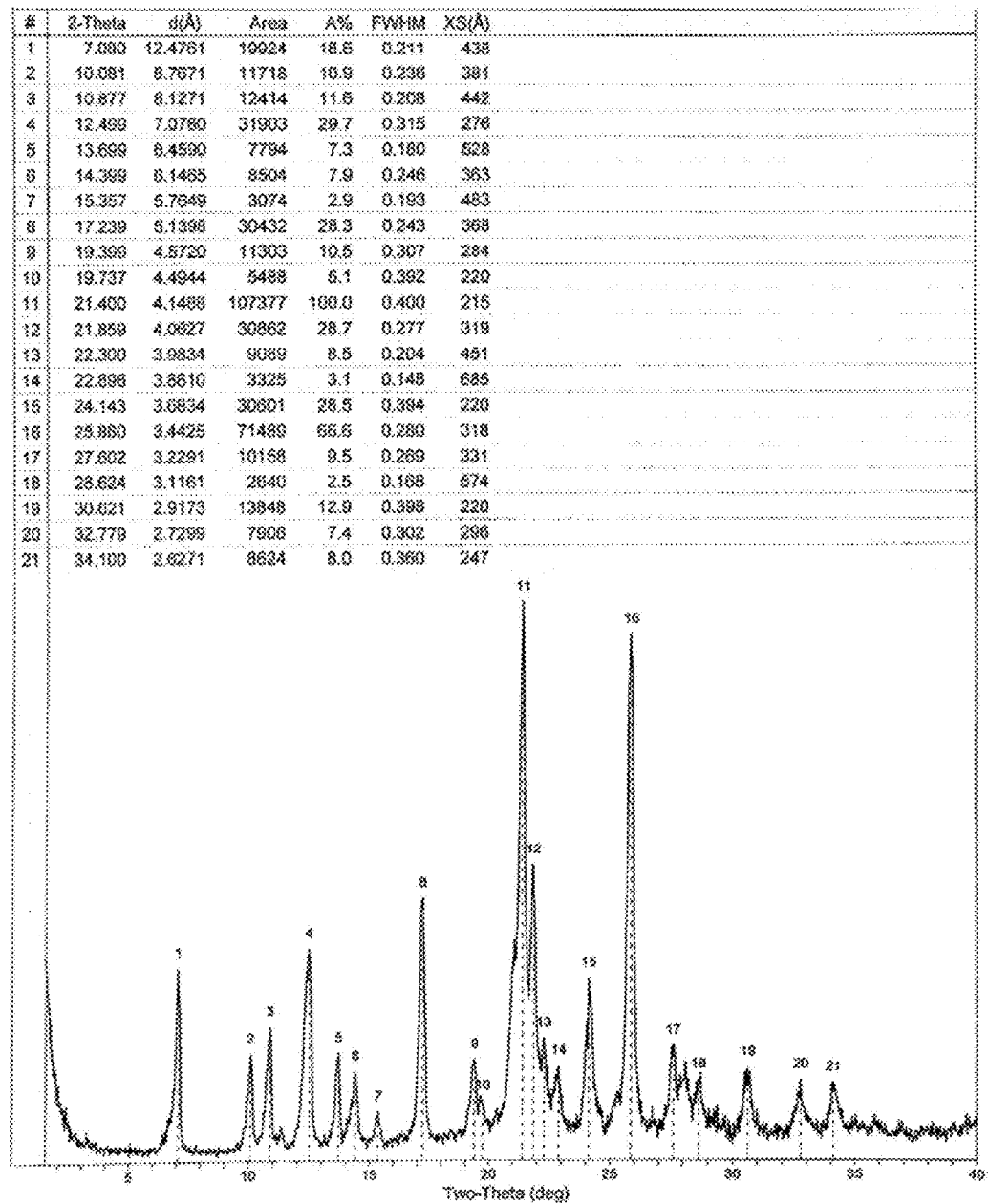
FIG. 1 is an XRPD spectrum for the sodium salt of the compound of formula A.

The technical solution of the present invention will be further described in detail with reference to specific examples. The following examples are merely illustrative and explanatory of the present invention and should not be construed as limiting the scope of the invention. All the techniques realized based on the above-mentioned contents of the present invention are covered by the protection scope of the present invention.

Unless otherwise specified, the raw materials and reagents used in the following examples are all commercially available products or can be prepared by known methods.

In the following examples, the detection conditions for the XRPD spectrum, the DSC-TGA curve, and the infrared absorption spectrum are as follows:

XRPD Detection Conditions:
  Instruments: Germany, BRUKER D2 PHASER powder X-ray diffractometer
  Conditions: Cu—Kα1 radiation, tube voltage 40 kV, tube current 150 mA, 2θ scanning range 1.5-40°, scanning speed 0.15°/second, and step size 0.02°.

DSC-TGA Detection Conditions:
  Instrument: Mettler Toledo thermal analyzer
  Conditions: initial temperature 30° C., temperature increased to 300° C. at a rate of 10° C./min, held for 27.5 minutes, and temperature increased to 400° C. at a rate of 10° C./min.

Infrared Absorption Spectrum:
  Instrument: PerkinElmer Spectrum100 infrared spectrophotometer.

Preparation Example 1: Preparation of the Compound of Formula A

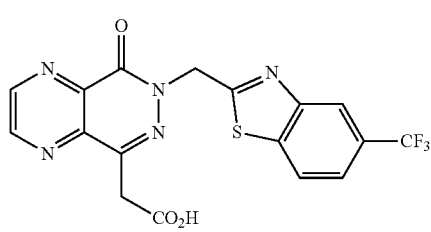

23.0 g of the compound represented by formula A was prepared by the method described in Example 1 of patent document CN201180034944.5.

Example 1: Preparation of the Sodium Salt of the Compound of Formula A (the Compound Represented by Formula A-N)

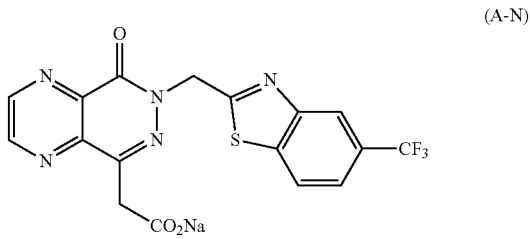

The compound of formula A (5.2 g, 12.35 mmol) and water (52 mL) were added to a reaction flask, stirred for 20 minutes, 10% sodium carbonate solution (7.2 mL, 6.79 mmol) was added at 10-25° C., the reaction solution was heated to 60-65° C., and the resulting mixture was reacted under stirring for 2 hours. The mixture was filtered, and the filtrate was cooled to 0-5° C. and allowed to stand for 12 hours while the temperature was maintained. The resulting mixture was filtered, and the filter cake was dried in vacuum at 45-60° C. for 20 hours to obtain the sodium salt of the compound of formula A (4.5 g, yield 82.2%).

$^1$H NMR (600 MHz, d6-DMSO) δ: 3.664 (s, 2H), 5.828 (s, 2H), 7.767-7.781 (d, 1H), 8.332-8.346 (d, 1H), 8.372 (s, 1H), 9.135-9.138 (d, 1H), 9.215-9.218 (d, 1H); $[M+H]^+$: 444.0353, $[M+Na]^+$: 466.0177; sodium content: 5.03% (theoretical value: 5.19%).

Figure 3:
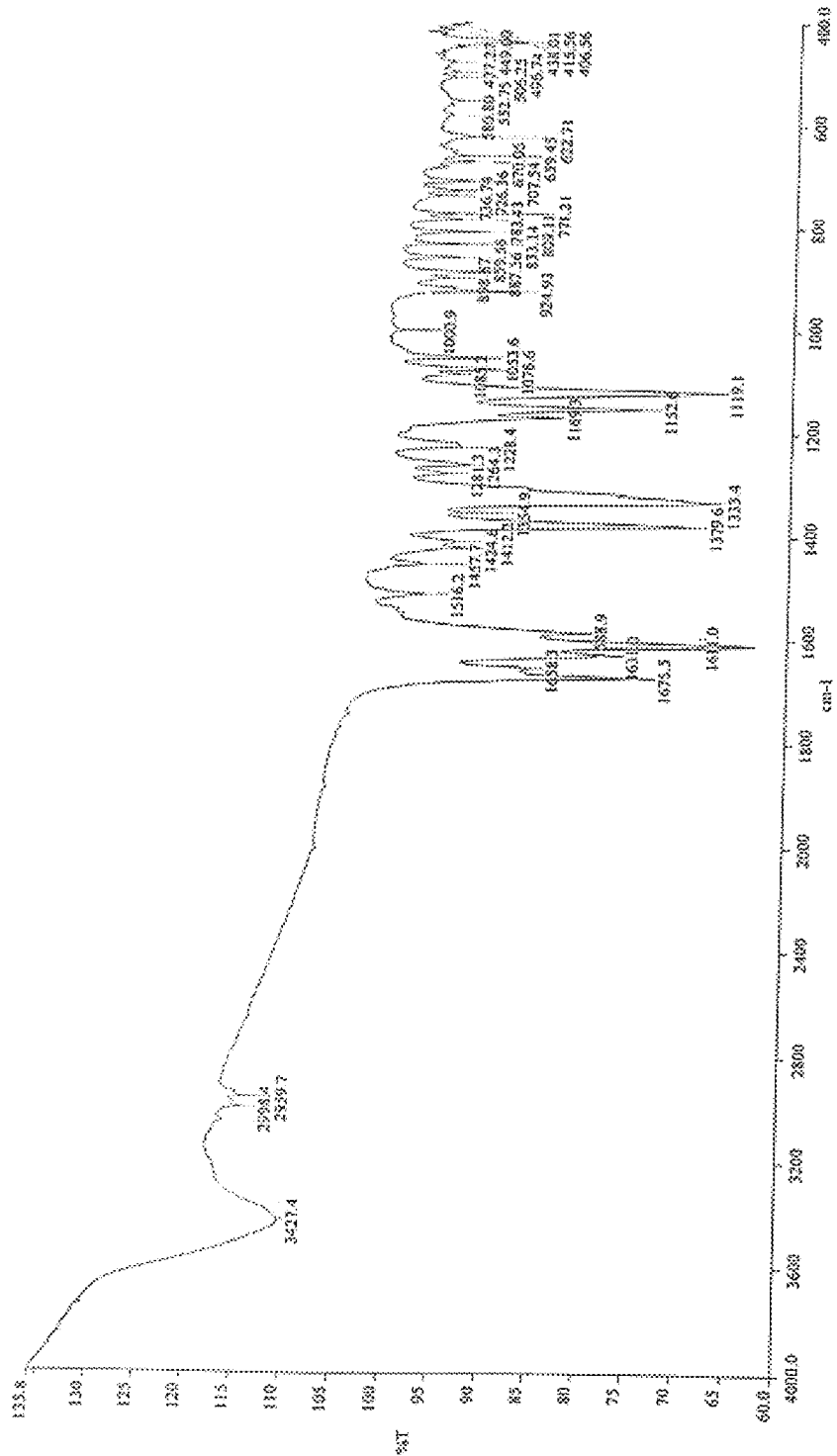
FIG. 3 is an infrared absorption spectrum for the sodium salt of the compound of formula A.

The infrared absorption spectrum is shown in FIG. 3, in which there are strong absorption peaks ($cm^{-1}$) at 1675.5, 1611.0, 1379.6, 1333.4, 1152.6 and 1119.1.

Figure 2:
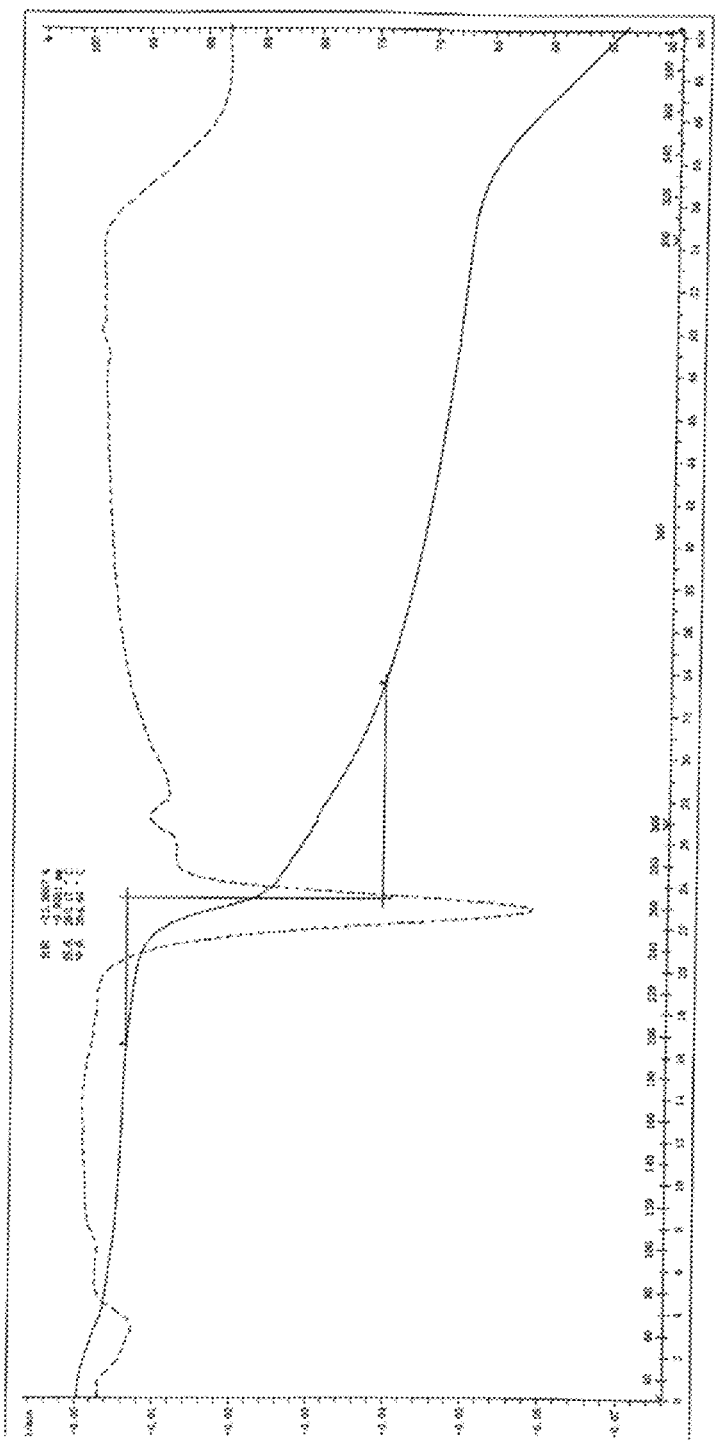
FIG. 2 is a combined differential thermal-thermal gravimetric analysis (DSC-TGA) curve for the sodium salt of the compound of formula A.

The obtained sodium salt exhibits good crystallinity, and its XRPD-characterized spectrum is shown in FIG. 1. The DSC-TGA detection result is shown in FIG. 2, and the detection result shows that the sample does not contain crystalline water or crystalline solvent, and the sample begins to significantly decompose at 260-270° C.

Example 2: Preparation of the Sodium Salt of the Compound of Formula A (the Compound Represented by Formula A-N)

The compound of formula A (5.2 g, 12.35 mmol) and water (52 mL) were added to a reaction flask, stirred for 20 minutes, 5% sodium hydroxide solution (10 mL, 12.5 mmol) was added at 10-25° C., the reaction solution was heated to 60-65° C., and the resulting mixture was reacted under stirring for 2 hours. The mixture was filtered, and the filtrate was cooled to 0-5° C. and allowed to stand for 12 hours while the temperature was maintained. The resulting mixture was filtered, and the filter cake was dried in vacuum at 45-60° C. for 20 hours to obtain the sodium salt of the compound of formula A (4.2 g, yield 76.7%). The obtained sodium salt exhibits good crystallinity, and its XRPD-characterized spectrum is substantially shown in FIG. 1.

Example 3: Preparation of the Sodium Salt of the Compound of Formula A (the Compound Represented by Formula A-N)

The compound of formula A (5.2 g, 12.35 mmol) and water (52 mL) were added to a reaction flask, stirred for 20 minutes, 20% sodium bicarbonate solution (5.7 mL, 13.57 mmol) was added at 10-25° C., the reaction solution was heated to 60-65° C., and the resulting mixture was reacted under stirring for 2 hours. The mixture was filtered, and the filtrate was cooled to 0-5° C. and allowed to stand for 12 hours while the temperature was maintained. The resulting mixture was filtered, and the filter cake was dried in vacuum at 45-60° C. for 20 hours to obtain the sodium salt of the compound of formula A (4.4 g, yield 80.4%). The obtained sodium salt exhibits good crystallinity, and its XRPD-characterized spectrum is substantially shown in FIG. 1.

Comparative Examples 1-5: Preparation of Other Salts of the Compound of Formula A (1) Preparation of Calcium Salt The compound of formula A (5.2 g) and water (52 mL) were added to a reaction flask, stirred for 20 minutes, 10% sodium carbonate solution (7.2 mL) was added at 10-25° C., the reaction solution was heated to 60-65° C., 10% aqueous calcium chloride solution (9.5 mL) was added, and the resulting mixture was reacted under stirring for 2 hours. The mixture was cooled to 0-5° C. and filtered, and the filter cake was dried in vacuum at 45-60° C. for 20 hours to obtain the calcium salt of the compound of formula A.

(2) Preparation of Magnesium Salt

The compound of formula A (5.2 g) and water (52 mL) were added to a reaction flask, stirred for 20 minutes, 10% sodium carbonate solution (7.2 mL) was added at 10-25° C., the reaction solution was heated to 60-65° C., 10% aqueous magnesium chloride solution (8.1 mL) was added, and the resulting mixture was reacted under stirring for 2 hours. The mixture was cooled to 0-5° C. and filtered, and the filter cake was dried in vacuum at 45-60° C. for 20 hours to obtain the calcium salt of the compound of formula A.

(3) Preparation of Alkaline Amino Acid Salt

With reference to the preparation method of Example 1, the preparation of alkaline amino acid salts: lysine salt, arginine salt, and proline salt of the compound of formula A was carried out using methanol as the reaction solvent.

(4) Preparation of Potassium Salt

With reference to the preparation method of Example 1 except for using potassium carbonate as the alkali, the potassium salt of the compound of formula A was obtained.

The experimental results for the above-mentioned comparative examples are as follows:

| Comparative Examples | Salt to be prepared | Experiment result |
|---|---|---|
| 1 | Calcium salt | White solid (4.8 g) was obtained. |
| 2 | Magnesium salt | White solid (4.7 g) was obtained. |
| 3 | Lysine salt | The obtained solid was too hygroscopic to exist stably. |
| 4 | Arginine salt | The obtained solid was too hygroscopic to exist stably. |
| 5 | Proline salt | The reaction solution was not changed and no salt was formed. |
| 6 | Potassium salt | White solid (4.9 g) was obtained. |

Comparative Examples 7-14: Investigation on the Method for Preparing the Sodium Salt of the Compound of Formula A With reference to the preparation method of Example 1, except that water as the reaction solvent was replaced with other solvents, and the alkali type and the reaction temperature were appropriately adjusted, the following experiment results were obtained:

| Comparative example | Reaction solvent | Alkali | Reaction temperature | Experiment result |
|---|---|---|---|---|
| 7 | Methanol 52 mL | 10% sodium hydroxide 10 mL | 55-60° C. | The solution turned black and no solid could be obtained |
| 8 | 1:1 (v:v) water-methanol, 52 mL | 10% sodium carbonate solution, 7.2 mL | 55-60° C. | The solution turned black and no solid could be obtained |
| 9 | 1:1 (v:v) water-methanol, 52 mL | 20% sodium bicarbonate solution, 5.7 mL | 55-60° C. | The solution turned black and no solid could be obtained |
| 10 | Ethanol, 52 mL | 10% sodium bicarbonate solution, 11.4 mL | 60-65° C. | The solution turned black and no solid could be obtained |
| 11 | 1:1 (v:v) water-ethanol, 52 mL | 10% sodium carbonate solution, 7.2 mL | 60-65° C. | The solution turned black and no solid could be obtained |
| 12 | 1:1 (v:v) water-ethanol, 52 mL | 10% sodium bicarbonate solution, 11.4 mL | 60-65° C. | The solution turned black and no solid could be obtained |
| 13 | 10:1 (v:v) water-acetone, 52 mL | 10% sodium bicarbonate solution, 11.4 mL | 50-55° C. | The solution turned black and no solid could be obtained |
| 14 | 10:1 (v:v) water-tetrahydrofuran, 52 mL | 10% sodium bicarbonate solution, 11.4 mL | 55-60° C. | The solution turned black and no solid could be obtained |

Test Example 1: Solubility Test

The salts obtained in Example 1, Comparative examples 1, 2 and 6, and the compound of formula A were tested for solubility in water, and the test method was as follows:

Test method: the samples to be tested were taken in a certain amount, gradually added to the purified water respectively, and continuously shaken until the samples reached the saturated state, the weighed amount of the samples to be tested and the used amount of the solvent were recorded, the concentrations at which the samples were dissolved were calculated, and the test results were shown in the following table:

| Example | Salt | Solubility (mg/mL) |
|---|---|---|
| Example 1 | Sodium salt | 10.05 |
| Comparative Example 1 | Calcium salt | Insoluble |
| Comparative Example 2 | Magnesium salt | Insoluble |
| Comparative Example 6 | Potassium salt | 5.67 |
| Compound of formula A | | 0.035 |

Test Example 2: Stability Test

The sodium salt of the compound of formula A obtained in Example 1 (packaging conditions: low-density polyethylene bag+polyester/aluminum/polyethylene composite bag for pharmaceutical packaging) was subjected to an accelerated test at 40° C.±2° C./75% RH±5% RH, and the results were as follows:

| Investigation items | 0 Month | 1 Month | 2 Month | 3 Month | 6 Month |
|---|---|---|---|---|---|
| Appearance | Off-white crystalline powder | Off-white crystalline powder | Off-white crystalline powder | Off-white crystalline powder | Off-white crystalline powder |
| Maximum single impurity (%) | 0.03 | 0.03 | 0.03 | 0.03 | 0.03 |
| Total impurity (%) | 0.40 | 0.45 | 0.37 | 0.42 | 0.54 |
| Moisture (%) | 0.6 | 0.7 | 0.7 | 0.8 | 0.8 |
| Content (%) | 100.8 | 99.6 | 99.9 | 99.6 | 100.9 |
| Crystal Form | XRPD as shown in FIG. 1 | | | | XRPD substantially as shown in FIG. 1 |

In conclusion, the sodium salt of the compound of the formula A according to the present invention had good solubility, low hygroscopicity, and stable quality, and was easier to be formed into a medicament relative to the compound of formula A or other salts of the compound of formula A.

The invention claimed is:

1. A crystal form of a compound represented by formula A-N,

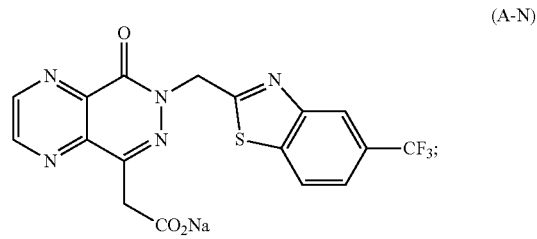

(A-N)

wherein said crystal form of the compound represented by formula A-N is characterized by an X-ray powder diffraction with characteristic peaks at 17.2±0.2°, 21.4±0.2°, 21.9±0.2°, and 25.9±0.2° expressed with 2θ angles by using the Cu—Kα radiation.

2. The crystal form of the compound represented by formula A-N according to claim 1, which is characterized in that said compound has an infrared spectrum, expressed as the reciprocal of the wavelength ($cm^{-1}$), with absorption peaks at 1675.5, 1611.0, 1379.6, 1333.4, 1152.6, and 1119.1.

3. The crystal form of the compound represented by formula A-N according to claim 1, wherein said crystal form of the compound represented by formula A-N is characterized by an X-ray powder diffraction with characteristic peaks at 7.1±0.2°, 12.5±0.2°, 17.2±0.2°, 21.4±0.2°, 21.9±0.2°, 24.1±0.2°, and 25.9±0.2° expressed with 2θ angles by using the Cu—Kα radiation.

4. The crystal form of the compound represented by formula A-N according to claim 3, wherein said crystal form of the compound represented by formula A-N is characterized by an X-ray powder diffraction with characteristic peaks at 7.1±0.2°, 10.1±0.2°, 10.9±0.2°, 12.5±0.2°, 13.7±0.2°, 14.4±0.2°, 17.2±0.2°, 19.4±0.2°, 21.4±0.2°, 21.9±0.2°, 24.1±0.20, and 25.9±0.2° expressed with 2θ angles by using the Cu—Kα radiation.

5. The crystal form of the compound represented by formula A-N according to claim 4, wherein said crystal form of the compound represented by formula A-N has an X-ray powder diffraction spectrum with the following characteristics by using the Cu—Kα radiation:

| # | 2-Theta | d(Å) | Area | A % | Full width at half maximum (FWHM) | Crystallite size XS (Å) |
|---|---|---|---|---|---|---|
| 1 | 7.080 | 12.4761 | 19924 | 18.6 | 0.211 | 438 |
| 2 | 10.081 | 8.7671 | 11718 | 10.9 | 0.236 | 381 |
| 3 | 10.877 | 8.1271 | 12414 | 11.6 | 0.208 | 442 |
| 4 | 12.499 | 7.0760 | 31903 | 29.7 | 0.315 | 276 |
| 5 | 13.699 | 6.4590 | 7794 | 7.3 | 0.180 | 528 |
| 6 | 14.399 | 6.1465 | 8504 | 7.9 | 0.246 | 363 |
| 7 | 15.357 | 5.7649 | 3074 | 2.9 | 0.193 | 483 |
| 8 | 17.239 | 5.1398 | 30432 | 28.3 | 0.243 | 368 |
| 9 | 19.399 | 4.5720 | 11303 | 10.5 | 0.307 | 284 |
| 10 | 19.737 | 4.4944 | 5488 | 5.1 | 0.392 | 220 |
| 11 | 21.400 | 4.1488 | 107377 | 100.0 | 0.400 | 215 |
| 12 | 21.859 | 4.0627 | 30862 | 28.7 | 0.277 | 319 |
| 13 | 22.300 | 3.9834 | 9089 | 8.5 | 0.204 | 451 |

-continued

| # | 2-Theta | d(Å) | Area | A % | Full width at half maximum (FWHM) | Crystallite size XS (Å) |
|---|---------|------|------|-----|-----------------------------------|-------------------------|
| 14 | 22.896 | 3.8810 | 3325 | 3.1 | 0.148 | 685 |
| 15 | 24.143 | 3.6834 | 30601 | 28.5 | 0.394 | 220 |
| 16 | 25.860 | 3.4425 | 71489 | 66.6 | 0.280 | 318 |
| 17 | 27.602 | 3.2291 | 10158 | 9.5 | 0.269 | 331 |
| 18 | 28.624 | 3.1161 | 2640 | 2.5 | 0.168 | 574 |
| 19 | 30.621 | 2.9173 | 13848 | 12.9 | 0.398 | 220 |
| 20 | 32.779 | 2.7299 | 7906 | 7.4 | 0.302 | 296 |
| 21 | 34.100 | 2.6271 | 8624 | 8.0 | 0.360 | 247. |

6. The crystal form of the compound represented by formula A-N according to claim 1, which is characterized in that said crystal form of the compound represented by formula A-N begins to significantly decompose at 260-270° C.

7. The crystal form of the compound represented by formula A-N according to claim 1, which is characterized in that said crystal form of the compound represented by formula A-N has a DSC-TGA curve with the following glass transition characteristics:

step: −22.3867%

−0.9051 mg onset: 260.17° C.

midpoint: 264.64° C.

8. A method for preparing the crystal form of the compound represented by formula A-N according to claim 1,

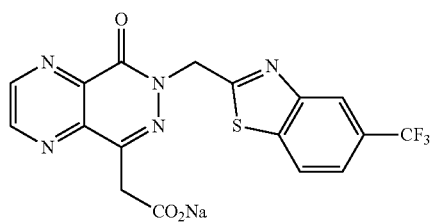

(A-N)

which is characterized in that the method comprises the following steps:

suspending a compound of formula A in water,

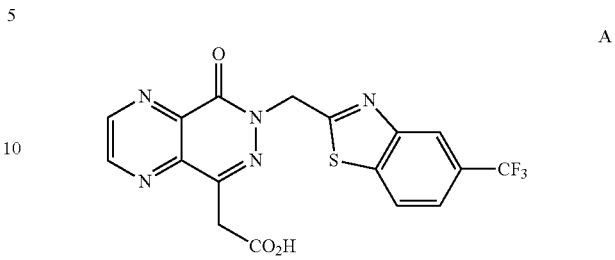

A wherein the mass volume ratio of the compound of formula A to water is 1:5-50;

adding an aqueous solution of an alkaline sodium compound to perform a salt forming reaction, wherein said alkaline sodium compound is selected from: sodium hydroxide, sodium carbonate, sodium bicarbonate, sodium methoxide, sodium ethoxide, sodium acetate, and sodium formate;

wherein said aqueous solution of the alkaline sodium compound has a mass volume concentration of 1-50%;

wherein the molar ratio of the alkaline sodium compound to the compound of formula A is 1-3.1;

wherein the temperature, at which the aqueous solution of the alkaline sodium compound is added, is 0-50° C.; and the reaction temperature of the salt forming reaction is 20-80° C.;

after the reaction is finished, the temperature is cooled to −5° C. to 10° C., the crystallization is stood for 8-24 hours;

separating solids, and drying to obtain the compound represented by formula A-N wherein the drying conditions include, the drying temperature is 40-70° C., the pressure is vacuum degree >0.090 MPa: the drying time is 10-50 hours.

9. A pharmaceutical composition, which contains the crystal form of said compound represented by formula A-N according to claim 1.

10. A method of treating a disorder in a patient by administering to the patient the crystal form of the compound represented by formula A-N according to claim 1, wherein the disease is selected from a group consisting of a cardiovascular disorder, an evolving myocardial infarction, atherosclerosis, coronary artery disease, diabetic nephropathy, diabetic neuropathy, and diabetic retinopathy.

* * * * *